United States Patent [19]

Dolling

[11] Patent Number: 4,605,761

[45] Date of Patent: Aug. 12, 1986

[54] PROCESS USING ACHIRAL CO-CATALYST PROMOTER FOR CHIRAL PHASE TRANSFER ALKYLATION PROCESS FOR AN ENANTIOMER OF A SUBSTITUTED FLUORENYLOXYACETIC ACID

[75] Inventor: Ulf H. Dolling, Westfield, N.J.

[73] Assignee: Merck & Co., Inc., Rahway, N.J.

[21] Appl. No.: 805,689

[22] Filed: Dec. 6, 1985

[51] Int. Cl.⁴ ............................................. C07C 69/94
[52] U.S. Cl. ..................................... 562/461; 560/53; 568/326; 568/327
[58] Field of Search ........................... 562/461; 560/53

[56] References Cited

U.S. PATENT DOCUMENTS

| | | | |
|---|---|---|---|
| 3,704,314 | 11/1972 | Cragoe, Jr. et al. | 562/461 |
| 3,903,145 | 9/1975 | Levine et al. | 562/461 |
| 4,070,539 | 1/1978 | Cragoe, Jr. et al. | 562/461 |
| 4,316,043 | 2/1982 | Cragoe, Jr. et al. | 562/461 |
| 4,317,922 | 3/1982 | Cragoe, Jr. et al. | 562/461 |

Primary Examiner—Paul J. Killos
Attorney, Agent, or Firm—Daniel T. Szura; Charles M. Caruso; Hesna J. Pfeiffer

[57] ABSTRACT

An improved method for the direct preparation of an enantiomer of a substituted fluorenyloxyacetic acid including the enhancement of a chiral phase transfer alkylation step in the synthesis using a non-ionic surfactant as co-catalyst. The substituted fluorenyloxyacetic acid is useful in the treatment of brain edema.

7 Claims, No Drawings

PROCESS USING ACHIRAL CO-CATALYST PROMOTER FOR CHIRAL PHASE TRANSFER ALKYLATION PROCESS FOR AN ENANTIOMER OF A SUBSTITUTED FLUORENYLOXYACETIC ACID

BACKGROUND OF THE INVENTION

The present invention is primarily concerned with a process for the efficient preparation of enantiomers of a substituted fluorenyloxyacetic acid.

Certain fluorenyloxyacetic acid useful for treating brain edema are disclosed in U.S. Pat. No. 4,316,043. These acetic acid have a chiral center and exist as racemates and individual enantiomers.

DESCRIPTION OF THE INVENTION

The present invention is concerned with a direct process for the efficient preparation of a substituted fluorenyloxyacetic acid which includes the step of forming a chiral center at an intermediate stage of the process by the alkylation of a hydrocarbonyloxy-6,7-dichloro-2-propyl-2,3-dihydro-1H-inden-1-one in the presence of chiral phase transfer catalyst and a significant amount of an achiral, non-ionic surfactant as co-catalyst. The presence of the surfactant during the chiral alkylation step is important to the efficient operation of the process. Although assymetric induction may be achieved in some degree by the use of the chiral catalyst by itself, the enantiomeric efficiency is enhanced by the addition of a relatively small amount of an achiral, non-ionic surfactant co-catalyst to the chiral phase transfer alkylation step of the process. Thus, by incorporating a non-ionic surfactant in the step, not only the amount of expensive chiral catalyst required is substantially reduced, but the reaction time is reduced and the ratio of desired isomer to undesired isomer increased without adversely affecting the yield of product obtained.

Thus, the process of the present invention useful in the preparation of a compound of the formula:

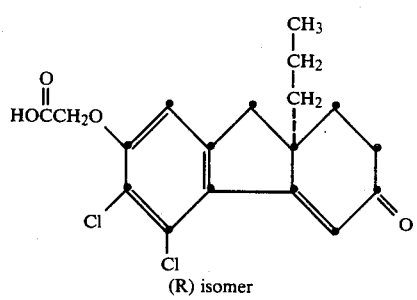

(R) isomer comprises:

(a) treating a compound of the formula:

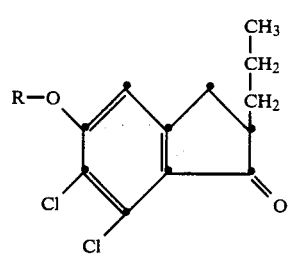

with 1,3-dichlorobutene-2 under liquid-liquid phase transfer condition in a basic medium in the presence of a chiral catalyst and an achiral, non-ionic surfactant co-catalyst to obtain a preponderance of the (R)-enantiomer of the trichloro ketone of the formula:

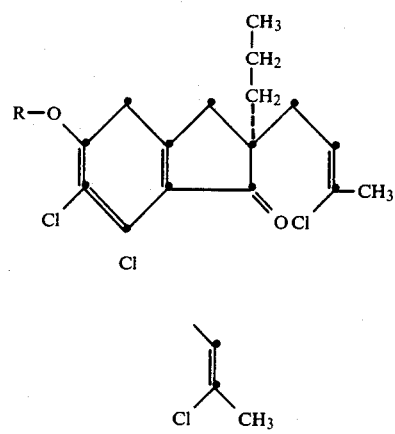

wherein R is a hydrocarbonyl radical selected from $C_1$-$C_6$-alkyl or phenyl $C_1$-$C_6$-alkyl;

(b) treating said trichloro ketone enantiomer with concentrated sulfuric acid and a small amount of water at a temperature of from 0°–25° C. to obtain a reaction mixture containing a-dichloro-diketone enantiomer of the formula:

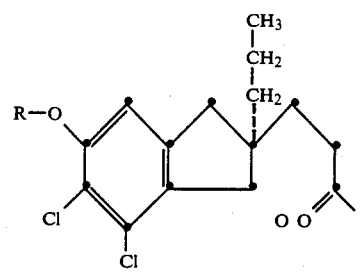

(c) increasing the temperature of the reaction mixture to effect cyclization and production of a fluorenone compound of the formula:

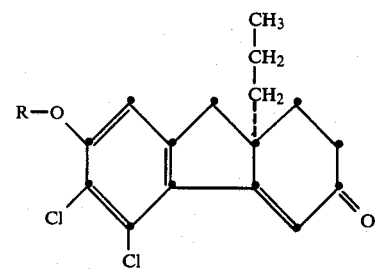

(d) treating said fluorenone compond with aluminum chloride to obtain a hydroxy-fluorenone compound of the formula:

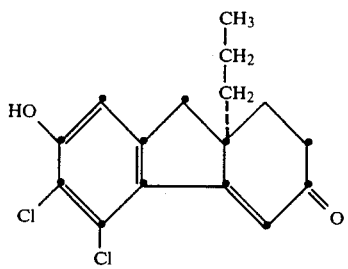

(e) treating said hydroxyfluorenone compound with a haloacetic ester in the presence of a base to obtain an oxyacetic acid ester derivative of the formula:

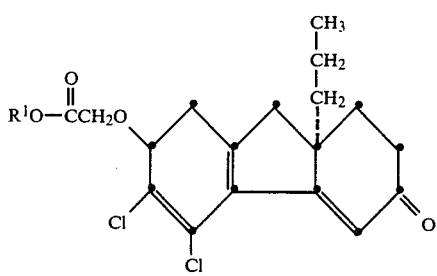

wherein $R^1$ is lower alkyl of from $C_1$–$C_6$;

(f) hydrolyzing said ester to produce a fluorenyloxyacetic acid compound of the formula:

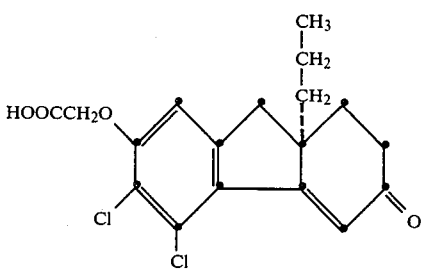

(g) and crystallizing said fluorenyloxyacetic acid compound to obtain the (R) isomer.

The chiral phase transfer alkylation of step (a) of the subject process is remarkably enhanced by the presence in the reaction mixture of a small amount, i.e., from about 1–10% by weight of an achiral non-ionic surfactant co-catalyst based on the weight of the starting indanone compound. When this step is compared to the process of asymmetric phase transfer alkylation with no surfactant added to the chiral catalyst, it is found that addition of a poly(ethylene glycol alkyl ether or alcohol) in the above indicated amounts, preferably about 4% by weight of the starting indanone, substantially reduces the reaction time, effects a higher enantiomeric efficiency (e.e.), reduces the amount of chiral catalyst required to ⅓ of the amount using no surfactant without adversely affecting the yield of alkylated indanone which is preferably not isolated, but used directly after washing out catalyst decomposition products, preferably as a toluene solution of compound III hereinabove.

In the next step (b), the solution of product III is hydrolyzed by treatment with concentrated sulfuric acid and sufficient water to provide 2 moles of water/mol of III with resultant production of compound IV. In step (d), the intermediate product IV is cyclized without isolation of compound IV by raising the temperature of the reaction mixture containing concentrated sulfuric acid to about 65°–75° C. to produce compound V in essentially quantitative yield.

The chiral catalyst employed in step (a), i.e., the chiral alkylation of the substituted indanone II is known to take place in the presence of approximately an equimolar amount of catalyst.

Any suitable chiral catalyst may be used and dihydro-N-benzylcinchonidinium or N-benzylcinchonidinium halide wherein benzyl is substituted or unsubstituted or wherein substituents (1 or 2) are selected from $CF_3$, halo, $C_1$–$C_3$, alkyl, $OCH_3$, CN, and the like including 3,4-dichlorobenzyl cinchonidinium chloride and p-trifluoromethyl cinchonidinium bromide is preferred. Dihydro-3,4-dichlorobenzyl cinchonidinium chloride and (ii) dihydro-p-trifluoromethyl benzyl cinchonidinium bromide can also be used if cleaved. Using these chiral catalysts, formula III compound containing the (R) isomer predominantly is obtained; the ratio of (R); (S) isomer will range from 75:25 to 90:10 higher.

As the co-catalyst promoter, any achiral non-ionic surfactant may be effectively used to enhance the chiral effect of the catalyst employed. Preferably the surfactants are poly(ethylene glycol, ethers and alchols). Such compounds are commercially available under the names Triton X (of the formula

wherein x is 3 to 70 Triton X-405 where is 40 or Triton X-100 where is 10), Triton N (of the formula $C_9H_{19}O$—$(CH_2$—$CH_2)_n OH$) where n is 4 to 100 poly(ethylene glycol) of mol wt. 200 to 1500, poly(ethylene glycol methyl ether) of mol wt. 350 to 1400 and the like.

The following examples are for purposes of illustration and are not in any way intended to set limits in the invention claimed. Temperatures are expressed in degrees Celsius unless otherwise noted.

EXAMPLE 1

Chiral Phase Transfer Alkylation 6,7-Dichloro-2-(3-chloro-2-butenyl)-2,3-dihydro-5-methoxy-2-propyl-1-H-inden-1-one (4)

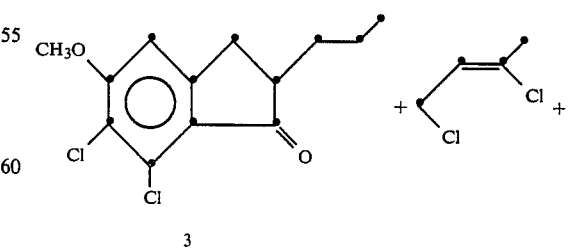

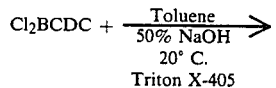

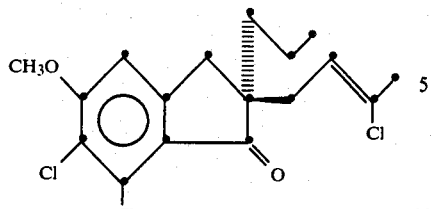

4

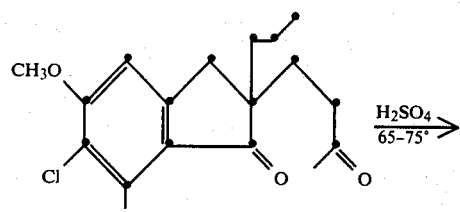

5

Materials 9.9 g; 36.2 mmole: 6,7-Dichloro-2,3-dihydro-5-methoxy-2-propyl-1H-inden-1-one (3)

15 g; 120 mmole: 1,3-Dichloro-2-butene (3.3 mole/mole of 3; DuPont, a 4/1 mixture of trans/cis-butenes)

5.4 g; 11 mmole: 3,4-Dichlorobenzylcinchonidinium chloride Cl$_2$BCDC; 30 mole % based on 3, N.B. β11967-288)

0.4 g: Triton X-405 (4 wt. % based on 3, Technicon Corp.; 70% aqueous solution)

300 ml: Toluene 60 ml: Sodium hydroxide, 50% aqueous solution

A 500 ml stirred autoclave was charged with 300 ml of toluene, 9.9 g of 3, 15 g of 1,3-dichloro-2-butene, 5.4 g of Cl$_2$BCDC, 0.4 g of Triton X-405 and 60 ml of 50% aqueous sodium hydroxide. The reactor was evacuated (22" Hg) and flushed with nitrogen three times. Then the mixture was vigorously stirred for 20 hours at 20° C. under 2-5 psi of nitrogen.

After completion the reaction mixture was transferred into a separatory funnel. The reactor was rinsed with a mixture of 180 ml of water and 100 ml of toluene which was combined with the reaction mixture. The opaque aqueous bottom layer was cut. The toluene layer was washed at room temperature with 100 ml 4N HCl/100 ml methanol, 100 ml 4N HCl and finally with 100 ml H$_2$O.

The final volume of toluene was 410 ml, containing 3.4 g of E-isomer of 4 and 9.8 g of Z-isomer of 4. The enantiomer ratio was 81/19 of (+/−) and the overall yield was essentially quantitative.

The experiment is repeated using p-Trifluoromethylbenzylcinchonidinium catalyst and the enantiomer ratio was 90/10 of (+/−) with essentially quantitative overall yield.

EXAMPLE 2

Hydrolysis and Cyclization 5,6-Dichloro-1,2,9,9a-tetrahydro-7-methoxy-9a-propyl-3H-fluoren-3-one (6)

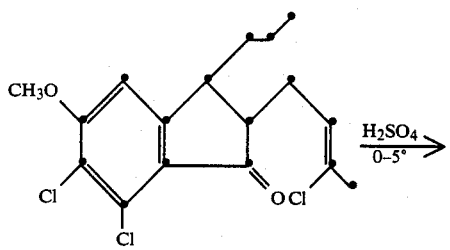

4

Materials 20 g; 55.3 mmole: 6,7-Dichloro-2-(3-chloro-2-butenyl)-2,3-dihydro-5-methoxy-2-propyl-1H-inden-1-one (4) (783 ml of a toluene solution, containing 25.55 mg/ml of 4; 80/20 enantiomer ratio).

55 ml: Concentrated; sulfuric acid 60 ml: 1N hydrochloric acid 2 ml: Water (2 moles/mole of 4)

160 ml: Toluene 200 ml: 5% Aqueous sodium bicarbonate

The solution of 4 in toluene from the last step was concentrated via distillation in a 250 ml 3 neck r.b. flask equipped with mechanical stirring, addition funnel and a distillation head to a total volume of 55 ml. At the end of the distillation the head temperature was 111°-112°. After distillation an N$_2$-inlet was connected to the flask and the stirred solution was cooled to 0° C. with an ice-methanol bath (bath temperature −10° C.). H$_2$SO$_4$ (50 ml) was added via the addition funnel at the rate of 10 ml/min maintaining a temperature range of 0°-5° with ice-methanol cooling. Complete addition of H$_2$SO$_4$ afforded a dark colored solution. The ice-methanol bath was replaced by an ice water bath and the reaction mixture was stirred at 0°-5° for 1.5 hours. Complete disappearance of starting material was observed by L.C.

At the end of 1.5 hours, the ice-cooling was removed and 2 ml of water was added over a period of 30 seconds to the reaction mixture. The temperature of the reaction mixture went up from 5° to 15° during the addition. The reaction mixture was heated to 60°-65° wherein a mild exotherm occurs and maintains the reaction of 65°-70° for about 30 minutes.

The reaction mixture was cooled to 25° C. and then slowly poured over 20 minutes into a stirred mixture of 150 ml of toluene and 275 ml of water allowing the temperature to rise to 35°. The residue in the flask was transferred successively with 5 ml concentrated H$_2$SO$_4$, and 2 times 10 ml of 1:1 mixture of toluene and water.

The heterogeneous mixture was stirred for 15 minutes at 50° and then allowed to separate at 50°. The bottom aqueous layer which has a slightly milky appearance was separated from the top toluene layer. The aqueous layer which contained 100 mg of product by L.C. assay was discarded. To the toluene layer containing the product was added 200 ml of a 5% sodium bicarbonate solution and the heterogeneous mixture was stirred for 60 minutes at 20°-25° and then allowed to settle. The bottom aqueous layer which has a slightly milky appearance was separated from the top toluene layer. The aqueous layer which contained 40 mg of product by L.C. assay was discarded. To the toluene layer containing the product was added 60 ml 1N HCl. The heterogeneous mixture was stirred for 30 minutes at 20°-25° and then allowed to settle. The bottom aqueus layer was separated from the top toluene layer. The aqueous layer which contained 16 mg of product by L.C. assay was discarded.

The top toluene layer containing the product was carried through to the next step. The wet toluene solution is stable and may be stored for several days without loss of product. The volume of the toluene solution was 200 ml containing 16.7 g (51.4 mmole, 93% yield) of product 6.

EXAMPLE 3

O-Demethylation 5,6-Dichloro-1,2,9,9a-tetrahydro-7-hydroxy-9a-propyl-3H-fluoren-3-one

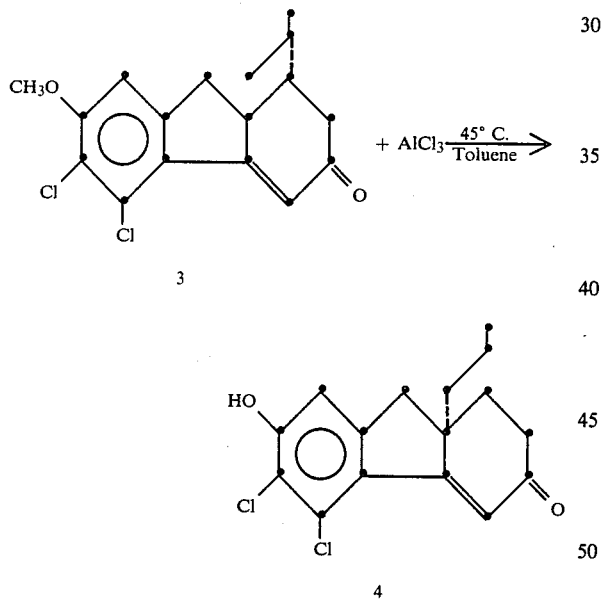

3

4

Materials 15.43 g; 47.4 mmole: Approximately 200 ml solution of 5,6-dichloro-1,2,9,9a-tetrahydro-7-methoxy-9a-propyl-3H-fluoren-3-one 3 in toluene.

22.1 g: 166 mmole: Aluminum chloride (3.5 moles per mole of 6)

34 ml: Water 30 ml: Toluene

The volume of the reaction mixture is adjusted to 230 ml with 30 ml of toluene. The toluene solution is dried by azeotropic removal of water at reflux to a KF of 0.1%. The solution is cooled to room temperature (20° C.) and the aluminum chloride is added over a period of 5 minutes. The temperature rises to 37° C. The mixture is heated to 45°-48° C. and aged at that temperature for 1.5 hours.

Completion of the demethylation is monitored by LC.

The reaction is quenched at 45°-47° C. by addition of 34 ml of water. The temperature rises to 75° C. The grey reaction mixture is then heated to reflux and aged at reflux for 1 hour. The reaction mixture is then dried by azeotropic removal of water.

EXAMPLE 4

O-Alkylation

[(5,6-Dichloro-2,3,9,9a-tetrahydro-3-oxo9a-propyl-1H-fluoren-7-yl)oxy]Acetic Acid Ethyl Ester

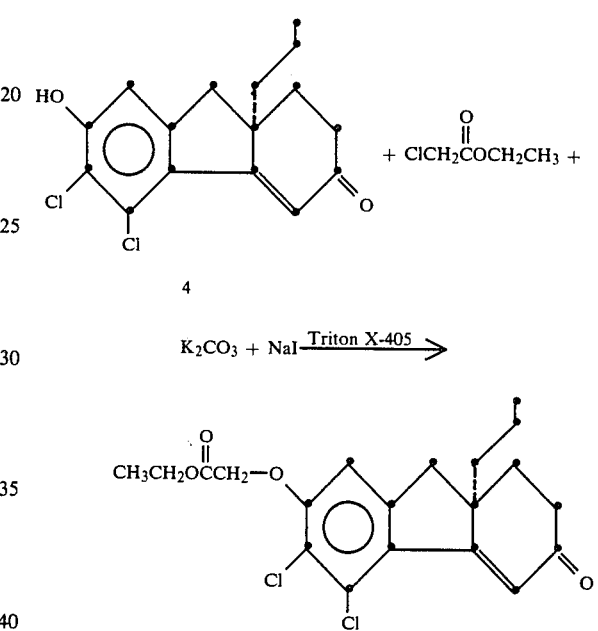

4

5

Materials

Approx. 14.7 g; 47.4 mmole: 5,6-Dichloro-1,2,9,9a-tetrahydro-7-hydroxy-9a-opyl-3H-fluoren-3-one approx. 230 ml of toluene.

3.9 g: Triton X-405, 25 wt.% based on Indanone 3.

29.5 g; 213 mmole: Potassium carbonate (1 mole per mole of aluminum chloride and 3 used in the previous step).

2.3 g; 15.3 mmole: Sodium iodide 9.57 g; 78.1 mmole: Ethyl chloroacetate 250 ml 2.5N Hydrochloric acid 250 ml 1.0N Hydrochloric acid To the reaction mixture from the previous step is added 3.9 g of Triton X-405, 29.5 g of potassium carbonate, 2.3 g of sodium iodide and 9.57 g of ethyl chloroacetate. The reaction mixture is heated to reflux and water is azeotropically removed. The reaction is aged for 4 hours at reflux while the water is removed. The reaction mixture is cooled to room temperature and 250 ml of 2.5N HCl is slowly added ($CO_2$ evolution!). The mixture is heated to 70°-75° C. and stirred for 0.5 hours. The bottom aqueous layer is cut at 70°-75° C. and discarded. The toluene layer containing the product is washed with 250 ml 1N HCl at 75° C. The toluene layer is cooled room temperature (20° C.). Yield 18.2 g (96.6% from 4).

EXAMPLE 5

Ester Hydrolysis

[(5,6-Dichloro-2,3,9,9a-*tetrahydro*-3-oxo-9-propyl-1H-fluoren-7-yl)oxy]Acetic Acid Potassium Salt

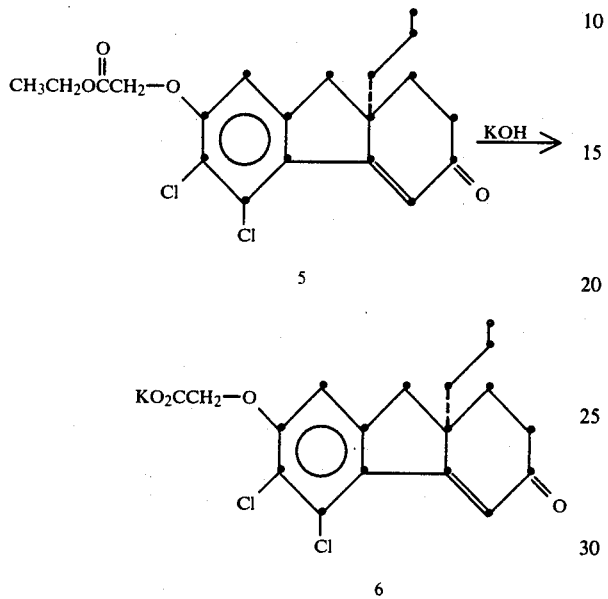

Materials

Approx. 18.2 g; 45.8 mmole: [(5,6-2,3,9,9a-tetrahydro-3oxo-9a-propyl-1H-fluoren-7-yl)oxy]acetic acid ethyl ester in approx. 230 ml of toluene from previous step.

101 ml: 1.17N Potassium hydroxide (2.5 mole KOH/mole of 8)

165 ml: Water

Water (165 ml) and 101 ml of 1.17N potassium hydroxide solution (2.5 mole KOH/mole of 5) are added to the toluene solution from the previous step. After mixing, the pH of the aqueous phase is 13.2. The mixture is refluxed for 2 hours and then cooled to 75° C. The bottom aqueous layer containing the product is separated and cooled to 20° C. Yield 15.7 g of 6 (as acid) (89.8% from 3), (R/S) Isomer ratio=80.5/19.5.

In the instance where p-trifluoromethybenzycinchonidinium catalyst is used as the catalyst the final product has an (R/S) isomer ratio of (90/10).

What is claimed is:

1. The process for the preparation of the formula:

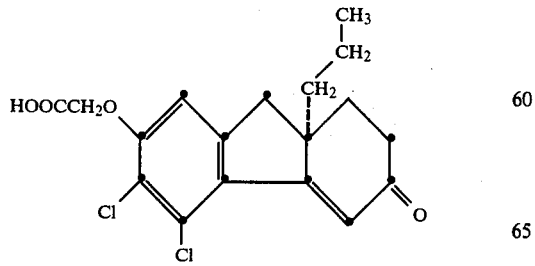

which comprises:

(a) treating a compound of the formula:

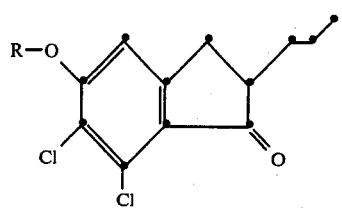

with 1,3-dichloro-2-butene under liquid-liquid base catalyzed phase transfer conditions in the presence of a chiral catalyst and an achiral, non-ionic surfactant co-catalyst to obtain a predominant amount of an enantiomer of the formula:

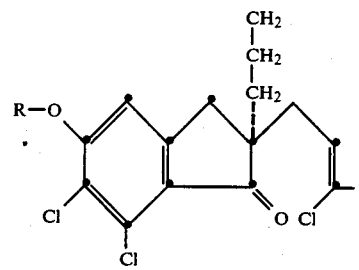

wherein R is a hydrocarbonyl radical selected from $C_{1-6}$ alkyl and phenyl $C_{1-6}$ alkyl;

(b) treating said enantiomer with concentrated sulfuric acid and water at a temperature of 0°–25° to obtain a reaction mixture containing a dichlorodiketo enantiomer of the formula:

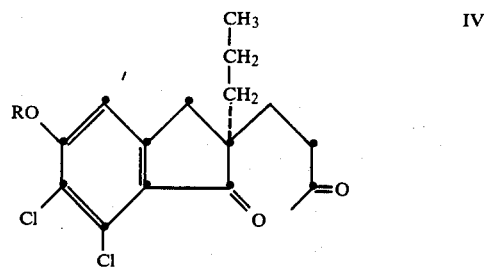

(c) raising the temperature of the reaction mixture to effect cyclization and production of a fluorenone compound of the formula:

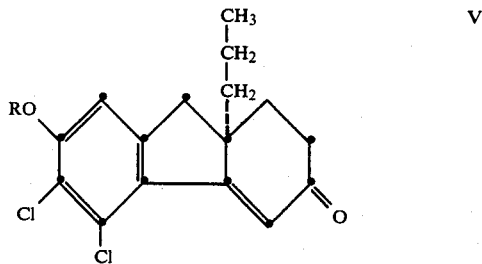

(d) treating said fluorenone compound with aluminum chloride to obtain a hydroxyfluorenone compound of the formula:

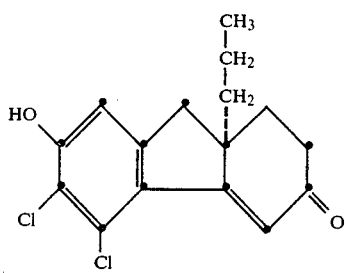

(e) treating said hydroxyfluorenone compound with a haloacetic acid ester in the presence of a base to obtain a fluorenyloxyacetic acid ester of the formula:

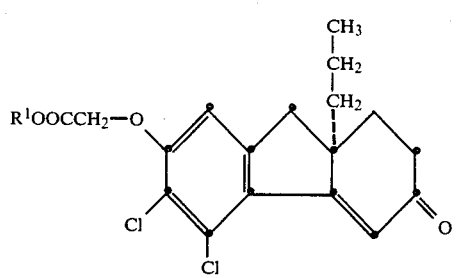

wherein $R^1$ is loweralkyl $C_1$–$C_5$;

(f) hydrolyzing said ester to produce a fluorenyloxy acetic acid of the formula:

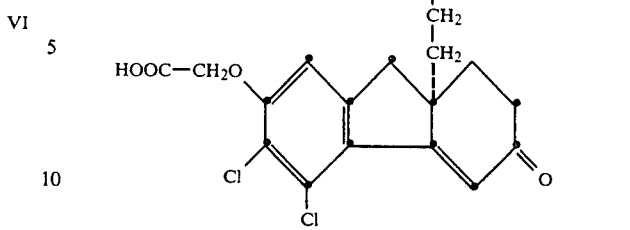

(g) and isolating said enantiomer I by crystallization.

2. The process of claim 1 wherein the chiral catalyst employed is 3,4-dichlorobenzylcinchonidinium chloride.

3. The process of claim 1 wherein the chiral catalyst employed in p-trifluoromethylbenzylcinchonidinium bromide.

4. The process of claim 1 wherein the achiral nonionic surfactant co-catalyst used is selected from polyethylene glycols, polyethylene glycol alkyl ether including ployethylene glycol methyl ether, and polyethylene glycol p-isoctylphenyl ether, or polymethylene glycol aryl ethers including polyethylene glycol p-nonylphenyl ether.

5. The process of claim 4 wherein the achiral nonionic surfactant used is Triton X-405 having the formula

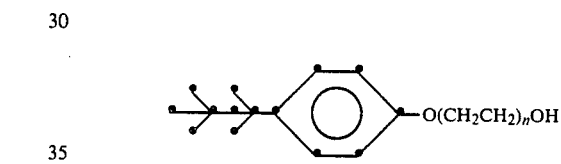

wherein n is 40.

6. The process of claim 5 wherein the achiral nonionic surfactant co-catalyst employed is from 1–10% by weight based on the indanone reactant.

7. The process of step a of claim 1.

* * * * *